United States Patent [19]

Smith

[11] Patent Number: 5,224,658
[45] Date of Patent: Jul. 6, 1993

[54] METHOD AND APPARATUS FOR RELEASING FLUID INCLUSION VOLATILES FROM ROCK SAMPLES

[75] Inventor: Michael P. Smith, Tulsa, Okla.

[73] Assignee: Amoco Corporation, Chicago, Ill.

[21] Appl. No.: 811,349

[22] Filed: Dec. 20, 1991

[51] Int. Cl.$^5$ .............................................. G01N 33/24
[52] U.S. Cl. ......................................... 241/27; 241/94; 241/270; 73/863.21
[58] Field of Search ...................... 73/38, 153, 863.22, 73/863.21, 863.31; 241/27, 84.4, 94, 270, 283

[56] References Cited

U.S. PATENT DOCUMENTS

| | | | |
|---|---|---|---|
| 11,368 | 7/1854 | Gardiner | 241/84.4 |
| 4,817,423 | 4/1989 | Christiansen | 73/153 |
| 4,856,351 | 8/1989 | Smith et al. | 73/863.21 |

OTHER PUBLICATIONS

"Mass Spectrometric Analysis of the Volatiles Released by Heating or Crushing Rocks" Analytical Methods Developed for Application to Lunar Samples Analyses, ASTM STP539, pp. 56–70 Barker et al., 1973.

Primary Examiner—Mark Rosenbaum
Assistant Examiner—John M. Husar
Attorney, Agent, or Firm—Richard A. Kretchmer; Frank J. Sroka

[57] ABSTRACT

Fluid-inclusion volatiles contained in a range of types of sedimentary rocks are released under uniform conditions by single-impact crushing by applying a force effective for releasing fluid-inclusion volatiles from unaggregated quartz-grain sands.

21 Claims, 3 Drawing Sheets

METHOD AND APPARATUS FOR RELEASING FLUID INCLUSION VOLATILES FROM ROCK SAMPLES

FIELD OF THE INVENTION

The invention relates to method and apparatus for releasing fluid-inclusion volatiles from rock specimens.

SETTING OF THE INVENTION

Composition analysis of fluid-inclusion volatiles in rock samples provides information useful for exploitation of reserves of oil, gas, and other minerals in the earth. Fluid inclusions are tiny cavities in mineral, 1 to 10 microns in diameter, containing liquid or gas trapped from ambient fluids present when the fluid inclusions were formed. Fluid inclusions are not part of the connected pore system of the formation and even in inclusion-rich rock may represent only about 0.1% of the rock volume. Analysis of the contents of fluid inclusions of a formation gives information about the environment when the fluid inclusions were formed, for example, whether the formation was of a type likely to have produced or accumulated hydrocarbons, or whether migration had occurred through the formation.

For bulk analysis of fluid inclusion volatiles, equipment used to release the fluid-inclusion volatiles from the rock samples should release and deliver substantially all of the fluid-inclusion volatiles from a rock sample to analysis. This permits comparison of variation in different composition parameters on a depth-by-depth basis.

To show such variation in fluid-inclusion compositions of subterranean rock as a function of depth along a borehole, it is necessary to be able to compare results of analysis from many different kinds of rocks ranging from carbonates to shales to sandstones.

In the past, the patterns of volatiles release for different kinds of rocks has varied greatly. For example, carbonates release a preponderance of fluid-inclusion volatiles on first impact over a range of crushing conditions. Quartz-grain sandstones, however, have sometimes required multiple impacts to assure an advantageous level of release of fluid-inclusion volatiles.

Even though effective release can be achieved by multiple-impact crushing of a wide variety of rock samples, other problems result. Multiple-impact crushing causes vibration and interferes in complex ways with background measurements and fluid-inclusion volatile measurements.

The invention is directed to apparatus and method which are effective for releasing fluid-inclusion volatiles under substantially the same operating conditions from different kinds of rocks so that the patterns of volatiles released as a function of time and operational state of the equipment are equivalent for the different kinds of rocks.

The invention hereinafter described is also directed in aspects to increasing the amount of volatiles released from certain types of rock samples and to improving effectiveness and efficiency of operation.

SUMMARY OF THE INVENTION

The invention relates to apparatus and method which release a preponderance of fluid-inclusion volatiles by single-impact crushing of rock samples over a wide range of sedimentary rock types from carbonates to poorly consolidated quartz-grain sandstones.

The invention relates to releasing fluid-inclusion volatiles from a rock sample and for delivering such volatiles to an outlet for analysis. A receptacle receives the rock sample and supports the rock sample during crushing. An enclosure encloses the receptacle and collects and delivers a volatiles sample released from fluid inclusions in the rock sample to an outlet of the enclosure. A crushing ram impacts the rock sample and releases fluid-inclusion volatiles from fluid inclusions in the rock sample. The crushing ram is effective for exerting an impact load effective for releasing substantially all, by volume, of fluid-inclusion volatiles from unconsolidated quartz-grain sand by single-impact crushing.

According to another aspect, the invention relates to apparatus and method for releasing fluid-inclusion volatiles from sedimentary rock samples where the crushing ram includes drive means for driving the crushing ram and means for maximizing the impact load exerted by the crushing ram on the rock sample at impact.

The following description and FIGURES set out other aspects of the invention.

DESCRIPTION OF THE INVENTION

Figure 1:
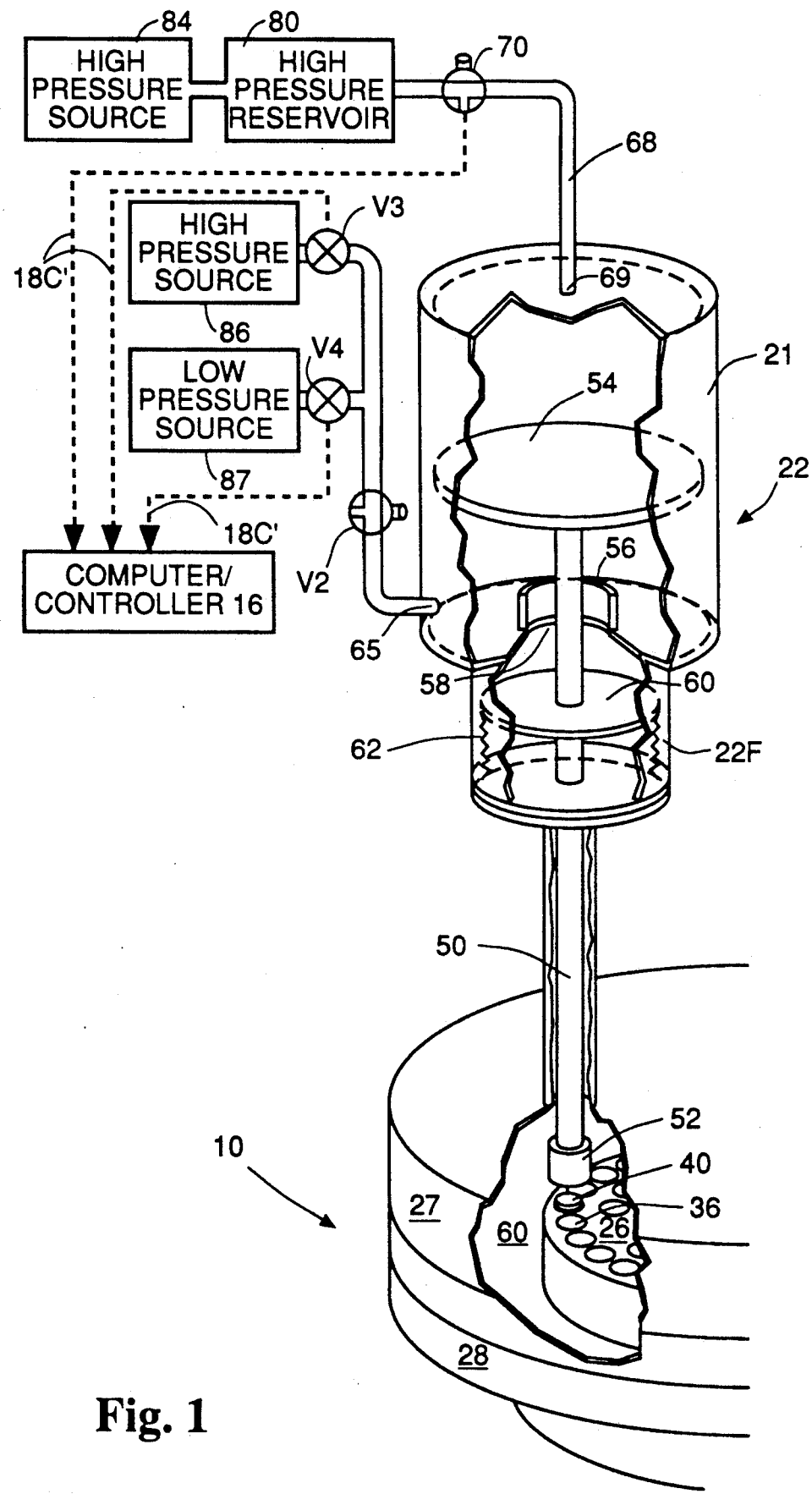
FIG. 1 illustrates a cutaway view of a portion of autosampler 10 of FIG. 2 illustrating a preferred embodiment of the invention.

The invention relates to apparatus and method for releasing a preponderance of fluid inclusion volatiles from a range of rocks by single-impact crushing.

Many kinds of rock present relatively little challenge to release of fluid-inclusion volatiles by single-impact crushing. These include carbonates, calcite, halite, salt, dolomites, fluorites and the like in which mineral hardness is typically much less than that of quartz. Quartz-grain sandstone is harder and more difficult to crush. Poorly consolidated quartz-grain sandstone has presented the greatest challenge among sedimentary rock types.

Loose quartz-grain sands having a size distribution comparable to those constituting sandstones can be taken as representative of the severest challenge. As such unconsolidated quartz-grain sands are crushed, the grains tend to distribute themselves in a close-packing configuration which absorbs and distributes the force applied without necessarily achieving a desired level of fluid-inclusion release from within the individual grains. The impact load to be exerted by the crusher system of the invention is therefore defined relative to loose quartz sand grains such as those having an average diameter of 250 microns or even less.

The problem of single-impact crushing has two parts. First, the force applied to quartz-grain sands must be sufficient to cause fracturing of the individual quartz grains and release of the desired level of fluid-inclusion volatiles. Second, when applied to sandstones, the force should be applied instantaneously in such a way as to take advantage to the extent feasible of the existing structure of the sandstone, before redistribution and repacking of the individual grains, to effect a greater release of fluid-inclusion volatiles. These effects are accomplished by maximizing the impact load during crushing relative to the static load exerted by the crusher after impact. Impact load is the force delivered by a blow, as opposed to a force applied gradually and maintained over a long period. At after-impact equilibrium this latter force is the static load.

In autosamplers such as described in European Patent Application 0 414 564 A2, pneumatic rams are used to effect crushing because pneumatic rams can readily be adapted with vacuum feedthroughs to process multiple rock samples in an evacuated chamber. The present invention is based on the discovery that the impact load of the crushing system of such autosamplers, when maximized, can be made effective for crushing unaggregated quartz-grain sands by single impact to release substantially all, by volume, of the fluid-inclusion volatiles therein. Substantially all means at least 75% by volume or even 90% or more by volume of the fluid-inclusion volatiles in a sample.

By providing such rams, the autosamplers can be operated over a wide range of rock types such as are encountered at different depths in a wellbore and can release substantially all fluid inclusions from each of the rock types by single-impact crushing. The pattern of release of fluid-inclusion volatiles can thus be made equivalent over the range of commonly encountered sedimentary rock types.

The results include a reduction in background noise and variability of results from different rock samples. Further, the amount of fluid-inclusion volatiles released from certain kinds of rocks, such as poorly consolidated sandstones, has been increased by a factor of as much as 100× or more compared to what previously could be achieved at ambient temperature even after multiple impacts. Even at elevated temperatures, for example, 150° C., as much as an order-of-magnitude improvement in release of fluid-inclusion volatiles has been observed.

Use of the invention has permitted use of ambient temperatures (21° C. to 37° C., typically about 26° C.) during operation of the autosampler. This ambient-temperature operation has been particularly significant in analysis of fluid-inclusion volatiles from sandstones.

Previously, use of elevated temperatures was favored because such temperatures overpressured fluid inclusions facilitating release. However, at the elevated temperatures, hydrocarbons present in the rock samples created high background levels which interfered with measurements of fluid-inclusion volatiles. Moreover, the relatively smaller release of fluid-inclusion volatiles from sandstones even at elevated temperatures, prior to this invention meant that the peak-to-background ratio for compounds of interest was low.

By using the autosampler according to the invention, and by operating at ambient temperature, the signal level from sandstones has been increased and the background level has been reduced resulting in greater precision and reliability of result.

According to one aspect of the invention, means are provided for maximizing impact load, relative to static load, of a ram crusher. This means is exemplified in particular reference to a crusher ram driven and retracted by a double-acting piston; but is also applicable to other piston-driven rams.

The means for maximizing impact load comprises in various aspects a reservoir adjacent the drive inlet port of the piston on the side where drive fluid is introduced to cause the piston to impact the rock sample. The reservoir has a reservoir volume of 2×, 5×, 10×, 100× or more the piston-displacement volume at maximum stroke. In this way, the pressure acting on the piston at impact has a maximum value substantially equal to the pressure in the reservoir irregardless of the piston-displacement volume.

The reservoir is closely adjacent the drive inlet port, generally within a few inches or feet and is connected in flow communication to the drive inlet port by a valved duct. The valve is preferably as close as feasible to the drive-inlet port.

The duct and valve have a flow diameter and length such that there is substantially instantaneous equilibration between the piston inlet and the reservoir. As used herein, substantially instantaneous equilibration means a period of time for reaching pressure equilibrium between the reservoir and the inlet chamber of the piston which is less than the time required for the impact stroke of the piston to be completed, preferably less than a fraction of such time such as ½ or 1/10 or even less.

Thus, by the time of impact by the piston-driven ram on the rock sample, the velocity of piston movement is at or approaching its maximum; and the pressure in the piston chamber is at or near its maximum. Hence, the impact load is substantially maximized for the piston-driven ram system.

Figure 2:
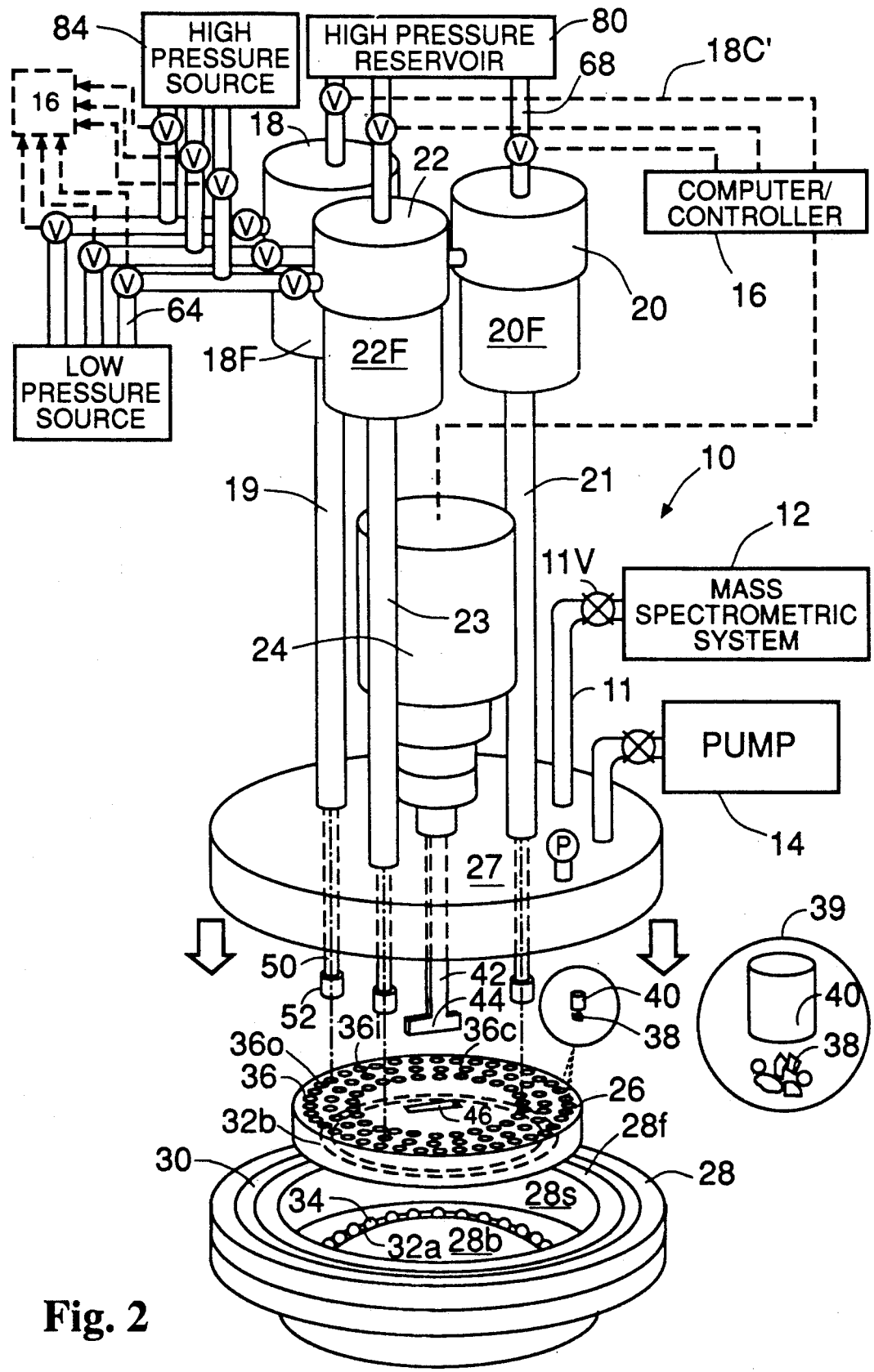
FIG. 2 illustrates, in exploded view, a preferred autosampler system in accordance with the invention for automated release to composition analysis of collective fluid-inclusion volatiles samples from each of a plurality of rock samples.

Referring now to FIG. 1, FIG. 1 illustrates a pneumatic-ram system for releasing fluid-inclusion volatiles in accordance with the invention. Reference to FIGS. 1 and 2 shows that the illustration of FIG. 1 is a portion of the system of FIG. 2 illustrating the pneumatic ram system in more detail. Reference numerals correspond in both FIGURES, except that valves in FIG. 2 are indicated simply by V but are given specific reference numerals in FIG. 1 to facilitate description.

The pneumatic-ram system illustrated comprises one or more drive fluid sources such as sources 84, 86, 87. Sources 84, 86, and 87 are illustrated as separate sources but of course two or more can be provided from a single source using an appropriate manifold. See, for example, FIG. 2. Preferably, drive fluid of at least two pressures is available: a high-pressure drive fluid for driving the piston during the downward, impact-effecting stroke; and a lower-pressure drive fluid for use as hereinafter described.

The high-pressure fluid can be any pressure effective for causing release of a preponderance of fluid-inclusion volatiles from quartz-grain sand on a single impact. Generally, a pressure of 50 psig or greater has been found effective, preferably about 110 psig or greater, using commercially available pneumatic rams. A static load on impact of about 400 pounds per square inch has been found advantageous. Actual impact time, the time during which the impact load is being exerted, is only a fraction of a second, ½ or 1/10 second or less.

The low-pressure drive fluid need be sufficient only for keeping the piston from falling due to the vacuum in chamber 60; and has a lower pressure than the high-pressure drive fluid so as to minimize cushioning effect due to drive fluid exiting lower piston housing prior to impact. A drive-fluid source delivering 15 psig pressure is very satisfactory, and higher or lower pressures can also be used.

As illustrated, a double-acting piston 54 is mounted for reciprocating movement in housing 22 by introduction of actuating fluid by duct 68 from source 84 or by duct 64 from other sources, such as sources 86, 87.

Duct 68 has a three-way controllable valve V1 connected to controller such as computer/controller 16 (See also FIG. 2) controlling operation of the valve in the operational sequence of the autosampler 10. Valve V1 can be a three-way valve connecting duct 68 either with source 84 or with a low-pressure environment such as ambient or atmospheric pressure.

Between source 84 and port 69 of housing 22 there is provided in accordance with the invention a certain volume illustrated as reservoir 80. Reservoir 80, ducts connecting source 84, reservoir 80, and port 69 are the inlet system to piston 54.

When valve V1 connects duct 68 with reservoir 80, drive fluid can enter housing 21 driving the action stroke of piston 54 until motion is stopped by impact with the rock sample or, if no sample is present, by stop ring 56 at maximum stroke. The geometric volume swept through by the piston is the displacement volume of the piston. According to the invention, the reservoir volume is $2\times$, $5\times$, $10\times$, $100\times$ or more the displacement volume of the piston to insure that the pressure acting on piston 54 at the time of impact of ramming tip 52 with the rock sample is substantially that of source 84. The ducts of the inlet system typically represent only a small fraction of the volume of the inlet system but must be sized so as not to permit significant pressure drop (i.e., >10%) during the action stroke.

During the action stroke of piston 54, rod 50 moves through opening 58 in housing 21 causing bellows 60 in feedthrough 22F to compress. Feedthrough 22F permits maintaining operating vacuum in chamber 60 of autosampler 10 during rod movement and crushing.

Rod 50, at its maximum downward extension, drives ram tip 52 into slug 40 covering a rock sample in receptacle 36 on carousel 26. Fluid-inclusion volatiles are released into chamber 60 defined by upper and lower housings 27 and 28 for delivery to composition analysis. See FIG. 2.

Immediately preceding the impacting stroke, valves V2, V3 and V4 are controlled by controller 16 to connect a lower pressure source 87 to the piston chamber below the piston. The lower pressure is effective for maintaining the piston in the retracted position, but does not create a high-pressure cushion for resisting the action stroke.

During impacting of a rock sample, the chamber existing in the piston housing below the piston is preferably exhausted to ambient or atmospheric pressure, for example, by lower port 65, duct 64 and three-way valve V2, again under control of controller 16. By venting the lower housing (already at reduced pressure) to atmospheric pressure during the piston action stroke, cushioning of the downstroke by trapped gases is minimized.

Following impacting, piston 54 is retracted. Piston 55 can be retracted by any suitable means such as springs or other mechanical means, magnetic, electromagnetic, vacuum, and the like. Preferably, piston 54 is retracted from the sample by introducing drive fluid into lower port 65 via source 86 or source 87, by controlling valves V2, V3, V4 in duct 64. Preferably, the retracting fluid is provided from a high pressure source such as source 87. During the retraction stroke, the housing 22 above the piston can be exhausted to ambient or atmospheric pressure via port 69, duct 68, and valve V1 to facilitate retraction.

After retraction of piston 54, high-pressure source 86 can be connected, or maintained connected, by controlling valves V2, V3, V4 in duct 64 to lower port 65 to prevent the vacuum in chamber 60 of autosampler 10 from pulling down piston 54 via feedthrough 22F during other operations of autosampler 10.

Referring now to FIG. 2, autosampler 10 includes upper housing 27 and lower housing 28 having seal 30 therebetween for forming an evacuable chamber 60 therebetween (see FIG. 1) when housings 27 and 28 are aligned and joined. Chamber 60 is desirably as small as feasible to minimize the volume which must be evacuated after each release of fluid-inclusion volatiles. Seal 30 can be an oxygen-free high-conductivity copper gasket. Housings 27 and 28 can be adapted with knife edges for sealing by engaging gasket 30. Evacuable chamber 60 has an outlet 11 with valve 11v which delivers released volatiles to analysis 12 as they are being released.

A vacuum pump such as pump 14 can place vacuum stage 10 under a vacuum at the start of a sequence of samples. Thereafter, the system can be maintained under vacuum by pumps (not shown) associated with the mass spectroscopic system 12; or by other pumps. The vacuum is generally maintained at about $10^{-8}$ to about $10^{-6}$ torr and does not exceed $10^{-6}$ torr even during fluid-inclusion volatile release.

Lower housing 28 comprises flange 28f, sidewall 28s, and base 28b. Base 28b has a groove 32 therein holding bearings 34. Circular carousel 26 is adapted with a plurality of sample chambers 36 therein and centered slot 46 for engagably receiving shaft key 44 on stepper motor shaft 42. Asymmetric tab 44 fits into notch 46 in the carousel. Asymmetry of tab 44 and notch 46 assure that the carousel 26 is positioned in the autosampler so that each sample has a uniquely determined position. Carousel 26 has groove 32b for engaging bearings 34 in groove 32a in base 28b. When carousel 26 is placed in lower housing 28, grooves 32b and 32a cooperate to align the carousel 26, and bearings 34 provide for rotation of carousel 26 in response to motor 24 turning shaft 42 having key 44 engagably connected with slot 46.

Sample chambers 36 are each effective for receiving a rock sample 38 and for maintaining it during volatiles release in a confined space between the walls and base of the receptacle chamber and the impacting means.

Individual rock samples 38 suitable for analysis generally range from about 1/100 to about ½ cc, typically about 1/25 to about ¼ cc. The samples can be any suitable rock sample, but are preferably drill cuttings taken as a function of depth along a wellbore. The samples can be heated overnight at a moderate temperature which does not cause thermal decrepitation of the fluid inclusions, either under vacuum or in air or in an oxygen-enriched environment to remove volatiles absorbed during drilling.

Three pneumatic rams 18, 20, and 22 are illustrated passing through upper housing 27. More or fewer rams can be used. Illustrated carousel 26 has three concentric rings of sample chambers 36 designated 36c, 36i, 36o. Each pneumatic ram aligns with a respective concentric ring of sample chambers. Ram 19 is illustrated with rod 50 and ram tip 52.

Figure 3:
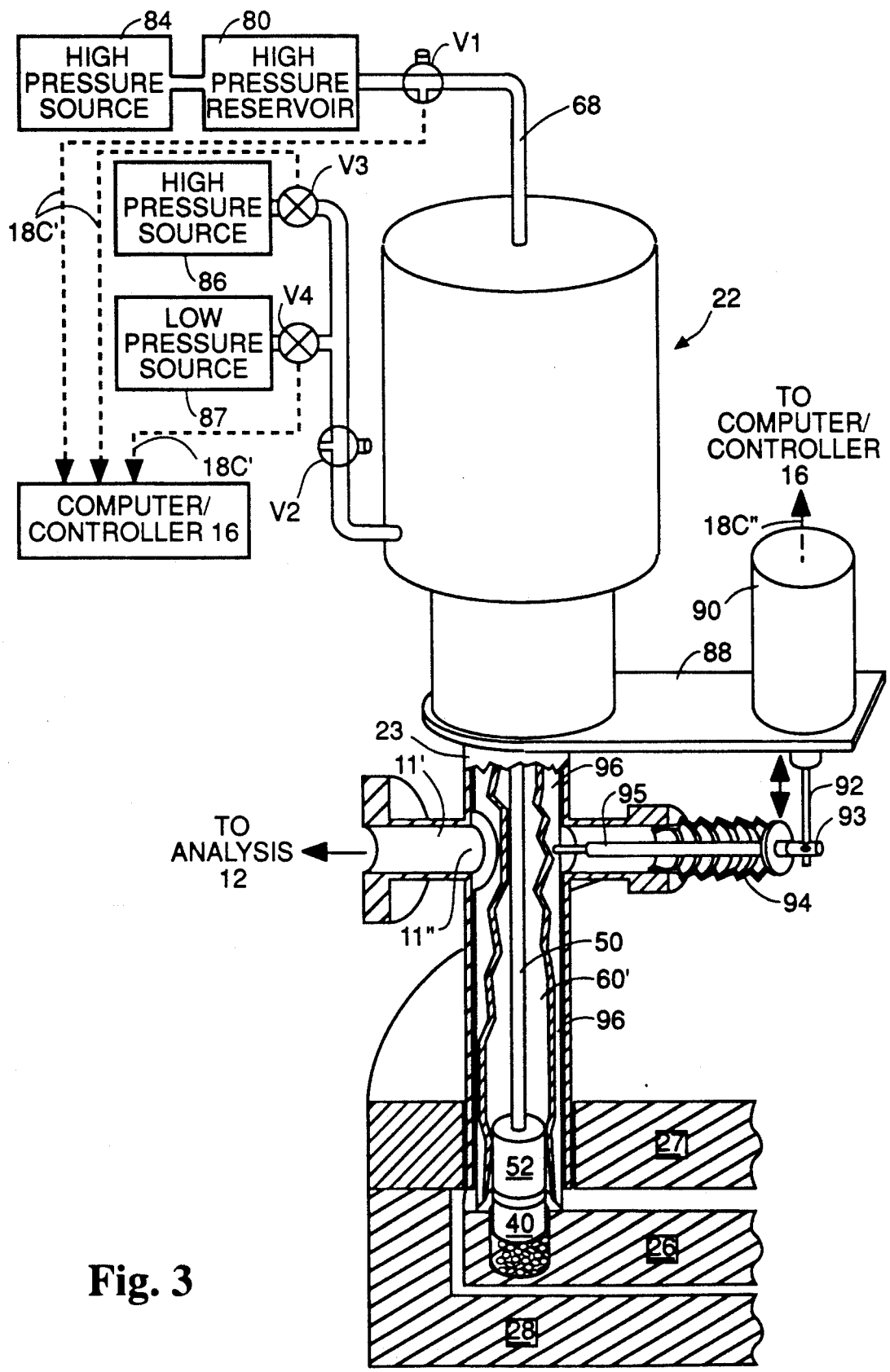
FIG. 3 illustrates an alternative embodiment of the FIG. 1 apparatus.

Referring now to FIG. 3, FIG. 3 illustrates that each of the rams can be provided with an engagable/retractable cylindrical sleeve or cylinder 96 surrounding the rod 50 which can be caused, for example, by solenoid 90 on support to engage a surface of carousel 26 adjacent a sample 36 prior to impacting the rock sample and to disengage from the surface following impact. Such a sleeve further reduces the volume 60' of the chamber into which fluid-inclusion volatiles are released and can also be used to channel or direct fluid-inclusion volatiles to analysis 12, for example, via opening 11" in sleeve 96 and conduit 11'.

During operation, prior to a ram such as ram 22 impacting a rock sample, solenoid 90 can be controlled by signal by line 18c" from computer/controller 16 to cause solenoid arm 92 coupled by coupling 93 to lever 95 in flexible housing 94 to drive the lower surface of sleeve 96 into contact with the surface of carousel 26. After impacting, solenoid 90 can be controlled to retract the sleeve.

Each of rams 18, 20 and 22 is controlled by computer/controller 16 via high pressure source 84 and reservoir 80 and low pressure source 64 as described herein.

When a sample chamber 36 is aligned with a respective ram, the ram is actuated to impact a sample 38 in the chamber effective for releasing a collective volatiles sample. Preferably, each sample chamber is provided with a sample chamber slug 40 to prevent cross contamination of samples during impacting. Slug 40 can be considered part of the impacting means. Sample 38 and slug 40 are shown enlarged in circle 39. However, slug 40 is adapted to cover sample 38 in chamber 36 while permitting volatiles to escape through an annulus between slug 40 and the wall of chamber 36. While only one slug 40 and sample 38 are shown, there will usually be as many slugs 40 and samples 38 as chambers 36.

Impacting of a sample preferably occurs while the sample is closely confined by a slug 40 in a chamber 36. According to the invention, the impact can be any impact sufficient for effecting an impact load over a nominal period of time such as one second for releasing substantially all, by volume, of fluid-inclusions volatiles for unaggregated quartz-grain sands, such as those having diameters of 250 microns or less.

After impacting, the static load can be released immediately or can be maintained for a period of time (10 seconds or even longer). It is preferred to maintain static load during analysis and to retract the ram only after completing analysis.

Then, referring to FIG. 1, computer/controller can cause valve V1 to be open to ambient pressure and cause valve V3 to open and valve V4 to close providing high pressure fluid via port 65 for returning piston 54 to its original retracted position.

Plates such as metal plates can if desired be used to separate samples 38 from each other in receptacle 36. The plates can be somewhat smaller in diameter than receptacle 36 and can be used to separate single layers of rock fragments. During impacting, released volatiles can migrate between the plates to the annular space at the periphery of receptacle 36 and through the annular space between the plates and chamber 36 to be delivered via space 60 to analysis. By using such plates, a significant increase in recovery of fluid-inclusion volatiles can be achieved from many rock samples; however, additional handling is required both before and after volatiles release.

Preferably, the gas fittings used in sampler 10 are flexible fittings and the mountings are resilient mountings to minimize or eliminate noise in signals due to vibration of the apparatus caused by impacting.

The invention has been illustrated in terms of a preferred embodiment, but is not limited thereto but by the following claims interpreted in accordance with law.

What is claimed is:

1. Apparatus for releasing fluid-inclusion volatiles from a sedimentary rock sample and for delivering released volatiles to analysis comprising:

a receptacle for receiving a sedimentary rock sample and for supporting the rock sample during crushing;

an enclosure for enclosing the receptacle and for collecting and delivering a volatiles sample released from fluid inclusions in the rock sample to an outlet of the enclosure;

crushing means for impacting the rock sample and for releasing substantially the entire volume of fluid-inclusion volatiles in the rock sample, the crushing means exerting an impact load having a magnitude effective for releasing by a single impact substantially all by volume of fluid-inclusion volatiles from unaggregated quartz-grain sand.

2. The apparatus of claim 1 wherein:

the crushing means is effective for exerting an impact load over a nominal period of time of one second or less and for releasing substantially all by volume fluid-inclusion volatiles from unaggregated quartz-grain sand having diameters of 250 microns or less.

3. The apparatus of claim 2 wherein:

crushing means comprises a plurality of fluid-pressure-actuated pistons;

each piston having a reservoir adjacent its drive fluid inlet having a reservoir volume greater than 2× the piston-displacement volume; and each drive-fluid inlet being connected to its reservoir by a duct having substantially no pressure drop therein.

4. The Apparatus of claim 1 for releasing fluid inclusion volatiles from a rock sample to an outlet for analysis comprising:

a plurality of receptacles within the enclosure for receiving a plurality of separate rock samples, each receptacle means for receiving a separate rock sample and for supporting each separate rock sample as each rock sample is individually crushed;

crushing means within the enclosure for individually impacting in sequence each rock sample of said plurality of rock samples, by single-impact crushing effective for releasing substantially the entire volume of fluid-inclusion volatiles therein from each rock sample.

5. The apparatus of claim 4 wherein crushing means comprises a double-acting piston and a fluid-pressure-drive system comprising:

means for controllably connecting a first drive-inlet port of the piston to one of a source supply of pressurized drive fluid and ambient air; and means for controllably connecting a second drive-inlet port of the piston to one of a first source supply of pressurized drive fluid, a second source supply of pressurized drive fluid, and ambient air.

6. The apparatus of claim 5 further comprising controlling means for controlling pressure experienced by the first inlet port according to a repeating sequence of source supply and ambient air; and controlling means for controlling pressure experienced by the second inlet port according to a sequence of first source supply, second source supply, and ambient air.

7. The apparatus of claim 4 wherein crushing means comprises a double-acting piston and a fluid-pressure-drive system including:
- a first source of drive fluid connectable to a first drive-inlet port of a first side of the piston for driving a rod attached to the piston to impact a rock sample;
- a second source of drive fluid connectable to a second drive-inlet port of a second side of the piston for retracting the rod after impacting the rock sample;
- a third source of drive fluid connectable to the second drive-inlet port, the second source comprising a higher pressure source than the second source; and
- means for sequentially controlling pressure experienced by each inlet port.

8. The apparatus of claim 7
wherein each of the first drive-inlet port and second drive-inlet port is controllably connectable to ambient pressure.

9. The apparatus of claim 7
wherein the first source of drive fluid comprises a source supply connectable via a reservoir of drive fluid and a valve-controllable duct to the first drive-inlet port.

10. The apparatus of claim 9
wherein the second source of drive fluid comprises a valve-controllable duct connecting the source supply to the second drive-inlet port.

11. Apparatus for releasing fluid-inclusion volatiles from a rock sample and for delivering released volatiles to analysis comprising:
- a receptacle for receiving a rock sample and for supporting the rock sample during crushing;
- an enclosure for enclosing the receptacle and for collecting and delivering a volatiles sample released from fluid inclusions in the rock sample to an outlet of the enclosure;
- a crushing ram within the enclosure for impacting the rock sample and for releasing a preponderance of fluid-inclusion volatiles from a sedimentary rock sample;
- wherein the crushing ram comprises a double-acting piston comprising a housing, a reciprocable piston therein defining a piston displacement volume, and first and second drive fluid inlets in the housing on first and second sides respectively of the reciprocable piston;
- drive means for driving the crushing ram;
- said drive means including means for maximizing impact load exerted by the crushing ram on the rock sample at impact;
- wherein the means for maximizing impact load comprises:
- a reservoir of drive fluid having a reservoir volume at least two times the piston displacement volume;
- reservoir delivery means for delivering drive fluid from the reservoir to the first side of the piston substantially without pressure drop; the apparatus comprising:
- first delivery means for delivering drive fluid of a first pressure to the second side of the piston;
- second delivery means for delivering drive fluid of a second pressure, lower than the first pressure, to the second side of the piston;
- exhaust means for exhausting fluid from the second side of the housing to ambient pressure; and
- means for controlling reservoir delivery means, first delivery means, and second delivery means for maximizing piston impact when drive fluid is delivered from the reservoir to the first side of the piston.

12. The apparatus of claim 11 wherein:
the piston-displacement volume at full stroke is less than one-half of the reservoir volume.

13. The apparatus of claim 11 wherein:
piston-displacement volume at full stroke is less than one-fifth of reservoir volume.

14. The apparatus of claim 11 wherein:
piston-displacement volume at full stroke is less than one-tenth of reservoir volume.

15. The apparatus of claim 11 wherein:
piston-displacement volume at full stroke is less than one-hundredth of reservoir volume.

16. The apparatus of claim 11 wherein:
the means for controlling is effective for providing drive fluid to inlet ports during operations of impacting, retracting, rest and pre-impact periods of the piston as follows.

| Piston State | Pressure at First Inlet Port | Pressure at Second Inlet Port |
|---|---|---|
| Impact | High | Ambient |
| Retract | Ambient | High |
| Rest | Ambient | High |
| Preimpact | Ambient | Low |

17. Method for releasing fluid-inclusion volatiles from a rock sample and for delivering released volatiles to analysis comprising:
- providing a receptacle for receiving a rock sample and for supporting the rock sample during crushing;
- providing an enclosure for enclosing the receptacle and for collecting and delivering a volatiles sample released from fluid inclusions in the rock sample to an outlet of the enclosure;
- placing a rock sample in the receptacle and evacuating the enclosure; and
- impacting the rock sample with a crushing ram exerting an impact load on the rock sample having a force effective for releasing a substantially all, by volume, fluid-inclusion volatiles by single-impact crushing from unaggregated quartz-grain sand.

18. The method of claim 17 for releasing fluid inclusion volatiles from a rock sample to an outlet for analysis comprising:
- placing a plurality of sedimentary rock samples in an enclosure in a plurality of receptacles each receptacle for receiving a separate rock samples and for supporting each separate rock sample as each rock sample is individually crushed;
- evacuating the enclosure;
- crushing within the enclosure in sequence each rock sample of said plurality of rock samples by single-impact crushing effective for releasing substantially the entire volume of fluid-inclusion volatiles therein from each rock sample.

19. The method of claim 18 wherein:
crushing is effected by a plurality of fluid-pressure-actuated pistons, each piston having a reservoir adjacent its drive fluid inlet having a reservoir volume greater than 2× the piston displacement volume; and each drive fluid inlet being connected to its reservoir by a duct having substantially no pressure drop therein.

20. The method of claim 19 wherein each piston comprises a double-acting piston and a fluid-pressure-drive system including:
   connecting a first source of drive fluid to a first drive inlet port of a first side of the piston for driving a rod to impact a rock sample;
   connecting a second source of drive fluid to a second drive inlet port of a second side of the piston for retracting the rod after impacting the rock sample;
   prior to repeating the foregoing steps, connecting a third source of drive fluid to the second drive inlet port, the third source being a lower pressure source than the second source; and
   repeating the foregoing steps.

21. Apparatus for releasing fluid-inclusion volatiles from a sedimentary rock sample and for delivering released volatiles to analysis comprising:
   a receptacle for receiving a sedimentary rock sample and for supporting the rock sample during crushing;
   an evacuable enclosure for enclosing the receptacle and for collecting and delivering a volatiles sample released from fluid inclusions in the rock sample to an outlet of the enclosure;
   engagable means for reducing volume within the enclosure into which fluid-inclusion volatiles are released;
   crushing means for impacting the rock sample and for releasing fluid-inclusion volatiles in the rock sample into the reduced volume of enclosure effected by the engagable means; and
   control means for directing a cooperative movement of said crushing means and said engagable means.

* * * * *